(12) United States Patent
Nguyen

(10) Patent No.: US 9,545,194 B2
(45) Date of Patent: Jan. 17, 2017

(54) MULTI-PURPOSE TROCAR WITH LENS CLEANER

(75) Inventor: Hien Tan Nguyen, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 375 days.

(21) Appl. No.: 14/232,974

(22) PCT Filed: Jul. 16, 2012

(86) PCT No.: PCT/US2012/046891
§ 371 (c)(1),
(2), (4) Date: Mar. 5, 2014

(87) PCT Pub. No.: WO2013/012790
PCT Pub. Date: Jan. 24, 2013

(65) Prior Publication Data
US 2014/0171739 A1     Jun. 19, 2014

Related U.S. Application Data

(60) Provisional application No. 61/508,346, filed on Jul. 15, 2011.

(51) Int. Cl.
| | | |
|---|---|---|
| *A61B 1/12* | (2006.01) | |
| *A61B 1/04* | (2006.01) | |
| *A61M 5/178* | (2006.01) | |
| *A61M 25/00* | (2006.01) | |
| *A61B 17/34* | (2006.01) | |
| *A61B 1/00* | (2006.01) | |

(Continued)

(52) U.S. Cl.
CPC .......... *A61B 1/126* (2013.01); *A61B 1/00154* (2013.01); *A61B 1/127* (2013.01); *A61B 1/3132* (2013.01); *A61B 17/0218* (2013.01); *A61B 17/3421* (2013.01); *A61B 17/3423* (2013.01); *A61B 90/70* (2016.02); *A61B 2017/3437* (2013.01)

(58) Field of Classification Search
USPC ........ 600/104, 106, 121–125, 156–159, 169; 604/158–163, 164.01–164.013, 604/167.01–167.06
See application file for complete search history.

(56) References Cited

U.S. PATENT DOCUMENTS

| 5,382,297 A | 1/1995 | Valentine et al. |
| 5,392,766 A | 2/1995 | Masterson et al. |

(Continued)

FOREIGN PATENT DOCUMENTS

WO     2008041225 A3     4/2008

*Primary Examiner* — Ryan Henderson
(74) *Attorney, Agent, or Firm* — Johns Hopkins Technology Ventures

(57) ABSTRACT

An embodiment in accordance with the present invention provides a scope lens cleaning system disposed within a trocar shaft to allow the surgeon to clean the scope lens without losing orientation of the operative field. The lens cleaning system is configured to remove solid debris, liquid, and condensation from the scope lens. The cleaning system includes a first cleaning component configured to remove the solid debris from the scope lens. A second cleaning component is configured to remove the liquid and condensation from the scope lens. A third cleaning component wicks the solid debris and liquid away from the cleaning components and the scope lens and allows it to fall out the end of the trocar shaft. The cleaning system minimizes distraction during the surgical procedure to improve efficiency and safety.

20 Claims, 5 Drawing Sheets

(51) Int. Cl.
*A61B 1/313* (2006.01)
*A61B 17/02* (2006.01)

(56) References Cited

U.S. PATENT DOCUMENTS

| | | | |
|---|---|---|---|
| 5,514,084 A | | 5/1996 | Fisher |
| 5,788,676 A | * | 8/1998 | Yoon .................. A61B 17/3462 604/164.01 |
| 6,354,992 B1 | | 3/2002 | Kato |
| 6,595,946 B1 | * | 7/2003 | Pasqualucci ....... A61B 17/3462 604/164.01 |
| 2002/0065450 A1 | | 5/2002 | Ogawa |
| 2006/0293559 A1 | | 12/2006 | Grice, III et al. |
| 2008/0051735 A1 | * | 2/2008 | Measamer ......... A61B 1/00087 604/265 |
| 2008/0058852 A1 | | 3/2008 | Ihde |
| 2008/0081948 A1 | * | 4/2008 | Weisenburgh ..... A61B 1/00135 600/121 |
| 2009/0234193 A1 | | 9/2009 | Weisenburgh, II et al. |
| 2009/0250081 A1 | | 10/2009 | Gordin et al. |
| 2009/0270817 A1 | * | 10/2009 | Moreno ............. A61B 17/3462 604/264 |
| 2010/0298775 A1 | * | 11/2010 | Berry ................ A61B 17/3421 604/167.03 |
| 2011/0152776 A1 | * | 6/2011 | Hartoumbekis ....... A61B 1/126 604/167.01 |

\* cited by examiner

MULTI-PURPOSE TROCAR WITH LENS CLEANER

CROSS REFERENCE TO RELATED APPLICATIONS

This application is a 35 U.S.C. §371 U.S. national entry of International Application PCT/US2012/046891 having an international filing date of Jul. 16, 2012, which claims the benefit of U.S. Provisional Patent Application No. 61/508,346, filed Jul. 15, 2011, the contents of each of the aforementioned applications is herein incorporated by reference in its entirety.

FIELD OF THE INVENTION

The present invention relates generally to surgery. More particularly, the present invention relates to a device and method for cleaning surgical tools during laparoscopic surgery.

BACKGROUND OF THE INVENTION

Laparoscopic and thorascopic surgery continues to become more prevalent and popular amongst surgeons and their patients. This minimally invasive approach allows patients to heal faster, with a shorter convalescence period and decreased risk for wound complications. However, the techniques required to perform laparoscopic surgery are difficult to master and often require additional time and training for a surgeon to master and become proficient. Therefore, it is common for a laparoscopic surgery procedure to take longer to perform in the operating room (OR), than the same case performed with a larger, open incision. With increasing literature supporting the merits of minimally invasive surgery, and with numerous, strong requests from patients, a surgeon often chooses to perform a minimally invasive procedure, despite the potential for a longer procedure time. It is therefore, paramount to find ways to shorten the procedure time for minimally invasive surgeries, while still providing the patient all of the benefits of the minimally invasive procedure.

Indeed, in an era of tightly-regulated managed care, and medical reimbursement, efficiency is critical. Surgeons who can perform an operation well, but in a shorter period of time, optimize their productivity by minimizing costs. In addition, at a typical cost of $30/minute for OR time, any time saved during the operation leads to direct cost savings, as well as indirect benefits, such as freeing up additional time and resources for the surgeon.

In all laparoscopic and thorascopic operations, one of the most time-consuming events is cleaning of the scope lens. The scope can become stained during any portion of the operation, for a variety of different reasons, including, but not limited to, direct tissue or fluid contact, smudging, or condensation which may occur naturally over the course of the surgery. When this happens, the surgeon must remove the scope from the trocar to clean it, typically, by wiping it down with a sterile cloth and applying an anti-fogging solution to minimize condensation. During this time, the surgeon is completely blind as to what is happening to the patient in the operating field. To continue the cleaning process, the surgeon must also wipe down the trocar port site, which is also likely stained from the fluid or debris that has been tracked through by the scope as it was removed. This requires additional time, and depending on the amount of staining, the trocar may need to be at least partially disassembled, so that it can be more thoroughly cleaned. After cleaning, the surgeon reinserts the scope through the clean trocar. However, the lens can quickly become stained again, obstructing the surgeon's vision and necessitating another cleaning. Each time the surgeon removes the lens for cleaning and subsequently reinserts, the surgeon must also reorient to the patient's anatomy. It also may be necessary to adjust anatomy in the surgical field.

It would therefore be advantageous to provide a device and method for the surgeon to clean the lens without having to fully remove the scope, during a minimally invasive surgical procedure.

SUMMARY OF THE INVENTION

The foregoing needs are met, to a great extent, by the present invention, wherein in one aspect, a cleaning system integrated into a trocar and configured to clean a lens of a scope to be disposed through the trocar, includes a first cleaning component configured for removing solid debris from the lens of the scope and disposed on an inside wall of the trocar, such that the lens of the scope and the first cleaning component can be brought into contact. A second cleaning component is configured for wiping fluid from the lens of the scope disposed on the inside wall of the trocar, such that the lens of the scope and the second cleaning component can be brought into contact. A third cleaning component is configured to wick the solid debris and fluid away from the lens of the scope, wherein the third cleaning component is disposed at a distal end of the trocar shaft.

In accordance with another aspect of the present invention the first cleaning component of the cleaning system takes the form of a brush. The brush further includes a saline spigot for cleaning the debris from the brush and the lens of the scope. The brush extends approximately halfway into the diameter of the shaft of the trocar. Further, the brush can include bristles configured to be elastic enough to allow for the passage of tools and the scope, but have tensile strength sufficient to remove the debris from the lens of the scope. The brush can also be dyed a color such that it is visible and identifiable.

In accordance with another aspect of the present invention, the second cleaning component takes the form of a sponge. The sponge is configured to collapse against an interior wall of the shaft of the trocar. A slidable switch is configured to collapse the sponge against the interior wall of the shaft of the trocar. When extended, the sponge extends approximately halfway into the diameter of the lumen of the shaft of the trocar. The sponge collapses to approximately less than 10% of the circumference of the shaft of the trocar. The sponge can also be dyed a bright color such that it is identifiable and visible. The third cleaning component includes grooves and can include at least three grooves.

In accordance with yet another aspect of the present invention, a trocar for performing laparoscopic surgery includes a housing defining a hub and a trocar shaft. The trocar shaft has a proximal end and a distal end and an outer wall defining a lumen extending therethrough, and the hub is coupled to the proximal end of the trocar shaft. An obturator is configured to be disposed through an opening in the hub of the trocar and through the lumen of the trocar shaft. The trocar includes a first cleaning component configured for removing solid debris from the lens of the scope and disposed on an inside wall of the trocar, such that the lens of the scope and the first cleaning component can be brought into contact. A second cleaning component is configured for wiping fluid from the lens of the trocar disposed on the inside wall of the trocar, such that the lens of the scope and the second cleaning component can be brought into contact. A third cleaning component is configured to wick the solid debris and fluid away from the lens of the scope, wherein the third cleaning component is disposed at the distal end of the trocar shaft.

In accordance with still another aspect of the present invention the first cleaning component of the trocar takes the form of a brush. The brush further includes a saline spigot for cleaning the debris from the brush and the lens of the scope. The brush extends approximately halfway into the diameter of the shaft of the trocar. Further, the brush can include bristles configured to be elastic enough to allow for the passage of tools and the scope, but have tensile strength sufficient to remove the debris from the lens of the scope. The brush can also be dyed a color such that it is visible and identifiable.

In accordance with another aspect of the present invention, the second cleaning component takes the form of a sponge. The sponge is configured to collapse against an interior wall of the shaft of the trocar. A slidable switch is configured to collapse the sponge against the interior wall of the shaft of the trocar. When extended, the sponge extends approximately halfway into the diameter of the lumen of the shaft of the trocar. The sponge collapses to approximately less than 10% of the circumference of the shaft of the trocar. The sponge can also be dyed a bright color such that it is identifiable and visible. The third cleaning component includes grooves and can include at least three grooves. The obturator further includes hollow regions configured and positioned to minimize friction between the obturator and the first and second cleaning components.

In accordance with still another aspect of the present invention, a method for cleaning a lens of a scope configured for use in a trocar includes moving the lens of the scope within an interior lumen of a shaft of the trocar. The method can also include removing debris from the lens of the scope with a first cleaning implement disposed within the shaft of the trocar. Additionally, the method includes removing fluid from the lens of the scope with a second cleaning implement disposed within the shaft of the trocar. The method also includes wicking the debris and fluid away from the lens of the scope and the lumen of the shaft of the trocar. This way the scope can be moved within the lumen of the shaft of the trocar without re-staining the lens of the scope with the debris or the fluid.

In accordance with yet another aspect of the present invention, the method further includes injecting saline through the first cleaning component to further clean the debris from the lens. An anti-fogging agent can also be injected through the first cleaning component to reduce condensation on the lens of the scope.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a scope lens cleaning system disposed within a trocar shaft to allow the surgeon to clean the scope lens without losing orientation of the operative field. The lens cleaning system is configured to remove solid debris, liquid, and condensation from the scope lens. The cleaning system includes a first cleaning component configured to remove the solid debris from the scope lens. A second cleaning component is configured to remove the liquid and condensation from the scope lens. A third cleaning component wicks the solid debris and liquid away from the cleaning components and the scope lens such that it can fall out the end of the trocar shaft. The cleaning system minimizes distraction during the surgical procedure to improve efficiency and safety.

Figure 1:
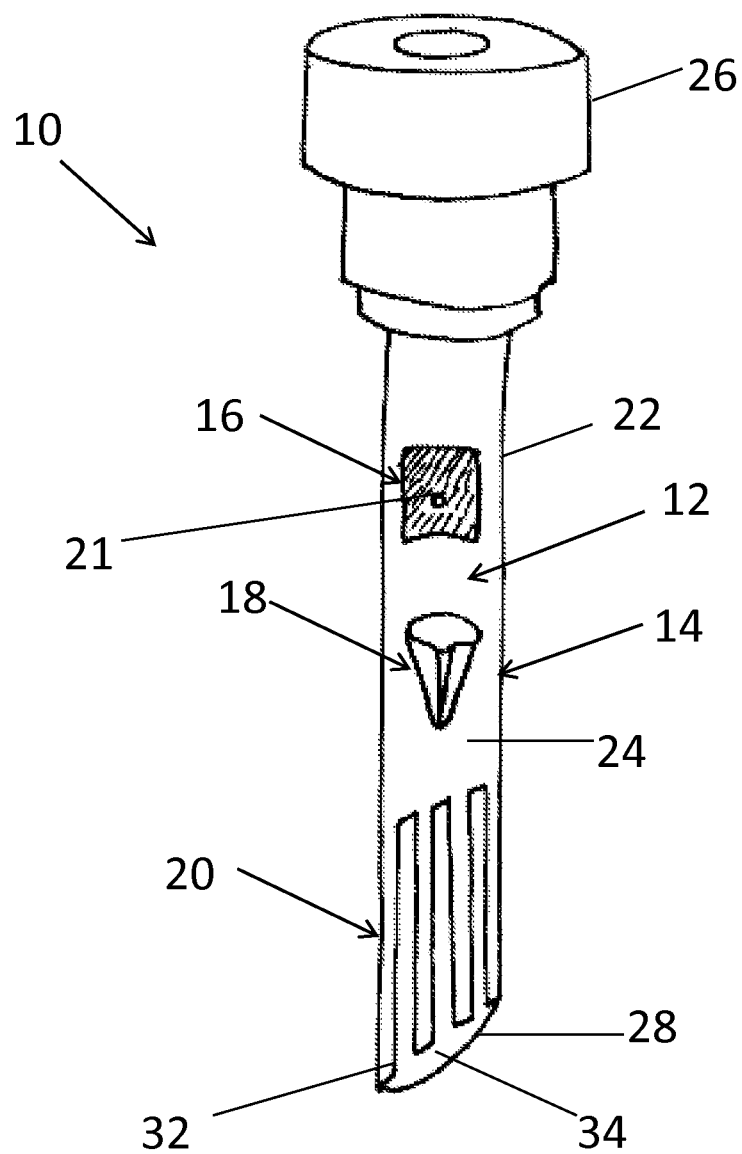
FIG. 1 illustrates a side view of a lens cleaning system disposed in a trocar, according to an embodiment of the present invention.
Figure 2:
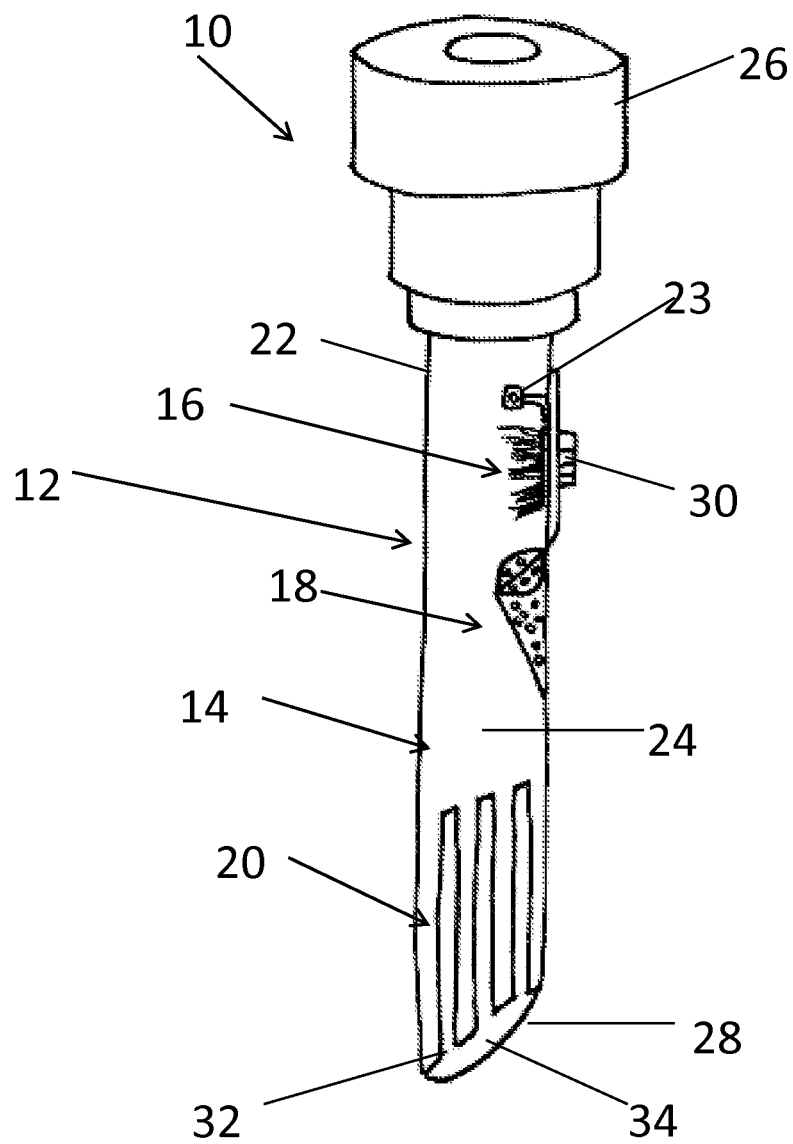
FIG. 2 illustrates a second sectional side view of the cleaning system for a scope lens, according to an embodiment of the present invention.

FIG. 1 illustrates a side view of a scope lens cleaning system disposed in a trocar and FIG. 2 illustrates a second side view of the cleaning system for a scope lens, according to an embodiment of the present invention. FIGS. 1 and 2 illustrate a trocar 10 having an integrated cleaning system 12 disposed within a shaft 14 of the trocar 10. Preferably, the trocar 10 takes the form of an approximately 12-mm trocar. However any suitable trocar known to or conceivable by one of skill in the art could be used. The trocar 10 should also be configured to receive a scope-type device, known to one of skill in the art, for performing laparoscopic and thorascopic procedures. The trocar 10 can be used with approximately 5 mm to 10 mm scopes having lenses disposed at 0, 30, and/or 45 degrees. Any other suitable scopes or lens configurations known to or conceivable by one of skill in the art could also be used with this cleaning system. The trocar 10 can also include an obturator, not shown, but commonly known to one of skill in the art. The obturator can have a bladeless point to separate layers of tissue, thus, allowing the surgeon to insert the trocar through the muscular layers. The top portion of the obturator can also be made with distinct hollow portions in order to minimize friction against the cleaning components described further herein.

The integrated cleaning system 12, illustrated in FIGS. 1 and 2, includes a first cleaning component 16, a second cleaning component 18, and a third cleaning component 20. The first cleaning component 16 is configured to remove solid debris from a scope lens (not pictured) during a minimally invasive laparoscopic or thoracoscopic procedure. The first cleaning component 16 can take the form of a brush or other suitable cleaning device known to or conceivable by one of skill in the art, for removing solid debris from the scope lens. The brush can be dyed a bright color for visibility and identification as the first cleaning component. The first cleaning component 16 can also include a spigot 21 such that a physician performing the surgery can inject saline to further clean the scope lens. Any other suitable solution could also be used, such as an anti-fogging agent to reduce condensation on the scope lens. A port 23 can be incorporated into a wall 22 of the trocar shaft 14, and can include a seal to prevent unwanted liquid from flowing through the spigot 21 and into an interior space 24 of the trocar shaft 14. The saline can be injected, for instance, using a syringe. However, any other suitable device known to one of skill in the art could also be used to inject the saline.

As illustrated in FIGS. 1 and 2, the first cleaning component 16 is situated closer to a proximal end 26 of the trocar 10. The brush of the first cleaning component can have a generally square shape, or any other suitable shape for removing the solid debris from the scope lens. The bristles of the brush can extend approximately one half of a diameter of the trocar shaft into the inner space 24 of the trocar shaft, and occupy approximately one quarter of the circumference. It should be noted that any other suitable configuration for the brush known to or conceivable by one of skill in the art could also be used. The bristles should be flexible enough to collapse flat against the inside wall of the trocar shaft 14 when the scope is passed through. However, the bristles should also have enough tensile strength to spring back to their original configuration to allow them to scrape the debris from the scope lens. In addition, the spigot 21 can be used to wash debris from the brush and also moisten the brush to more effectively clean the scope lens.

With respect to FIGS. 1 and 2, in an embodiment of the present invention, included herein simply as an example to further illustrate the design and function of the present invention and is not meant to be limiting, the brush forming the first cleaning component 16 is of a rectangular design, measuring approximately 7 mm in width and 10 mm in length with a spigot embedded within the center. The spigot head 20 is flush with the side of the trocar shaft 14, in order to prevent the scope from catching on it during insertion through the trocar shaft. The short bristles of the brush measure approximately 3-4 mm which is enough to scrape solid debris from the lens of the scope without being obstructive to items being inserted through the trocar. The bristles can be formed from a surgery-grade plastic, or any other suitable material known to or conceivable by one of skill in the art.

As illustrated in FIGS. 1 and 2, the second cleaning component 18 takes the form of a sponge attached to an inside surface of the wall 22 of the trocar shaft 14. While the details of a sponge are discussed below, it should be noted that any other suitable cleaning device could also be used. The second cleaning component 18 can be dyed a distinct bright color from the first cleaning 16 component for visibility and easy distinction between the two components. The sponge is configured to wipe away any fluid remaining on the lens after it has been cleaned by the brush. The sponge can also be used to wipe away any condensation that may have formed on the scope lens during the surgical procedure.

As illustrated in FIGS. 1 and 2, the sponge, or second cleaning component 18, is positioned distal to the first cleaning component 16, closer to the distal end 28 of the trocar shaft 14. In some embodiments, that will be discussed further herein, the sponge can be collapsible. The collapsibility of the sponge allows it to serve at least two purposes. First, it minimizes the bulk of the sponge and allows the scope to pass through the trocar, unhindered. Second, it rings the moisture out of the sponge, allowing it to be re-used more effectively. In the collapsed state, the sponge can take up less than approximately 10%, or 1 mm of the circumference of an exemplary 12-mm trocar. Collapse and deployment of the sponge can be controlled with a switch 30 positioned near a head of the trocar, as discussed further with respect to FIGS. 3 and 4.

The third cleaning component 20 is illustrated in FIGS. 1 and 2 as a set of grooves 32 positioned near the distal end 28 of the trocar shaft 14. These grooves 32 allow the accumulated fluid and debris within the trocar to effectively wick away from the first and second cleaning components 16 and 18 and fall out of the trocar shaft 14, such that the first and second cleaning components 16 and 18 can be re-used throughout the surgical procedure. These grooves 32 also allow for a clean opening 34 at the distal end 28 of the trocar shaft 14 to prevent re-staining of the scope lens as it is passed back into the surgical field. The grooves 32 can be approximately 1 mm in width by approximately 4 mm in length. However, any suitable length and width could also be used. The grooves 32 also prevent beading of fluid at the tip of the trocar shaft 14, which can re-stain the lens.

Figure 3:
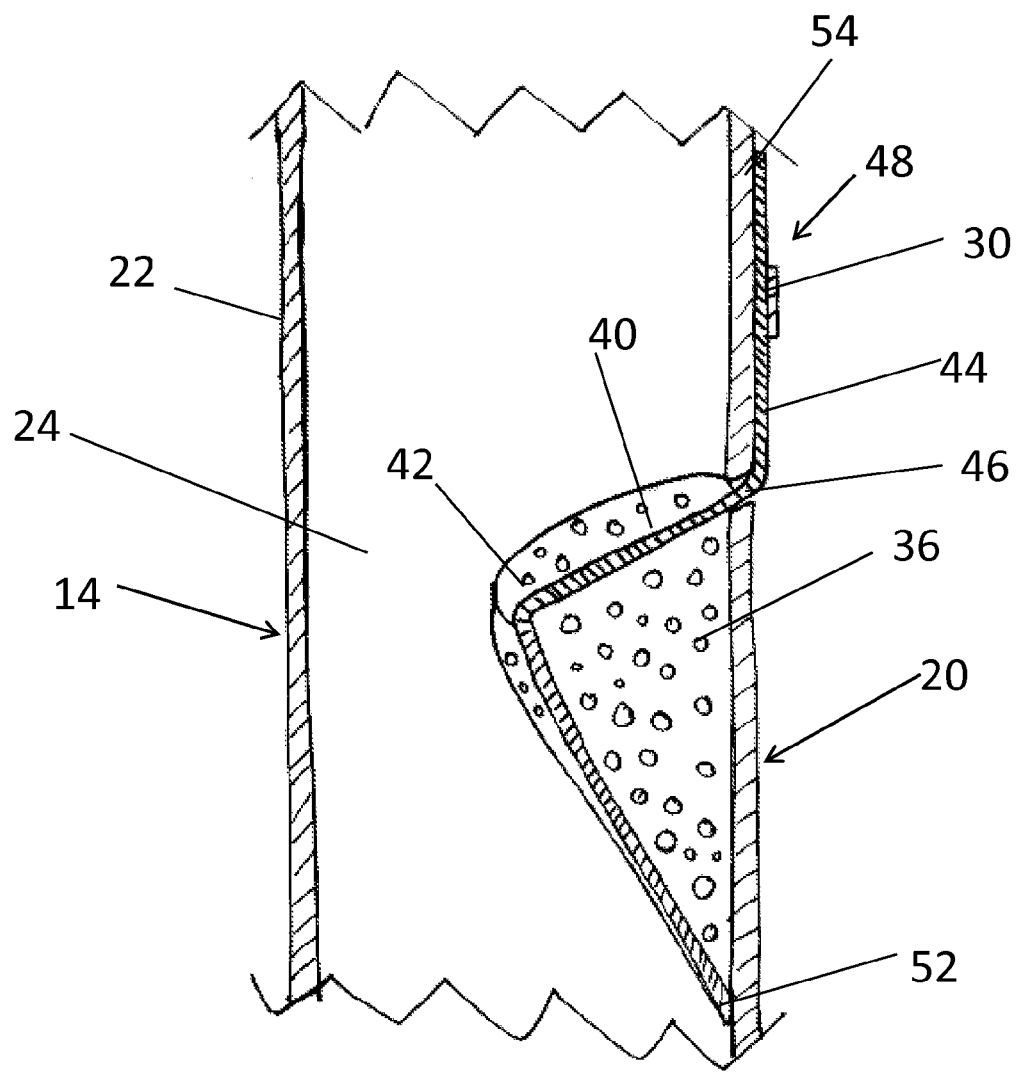
FIGS. 3 and 4 illustrate partially sectional views of a second cleaning component according to an embodiment of the present invention.
Figure 4:
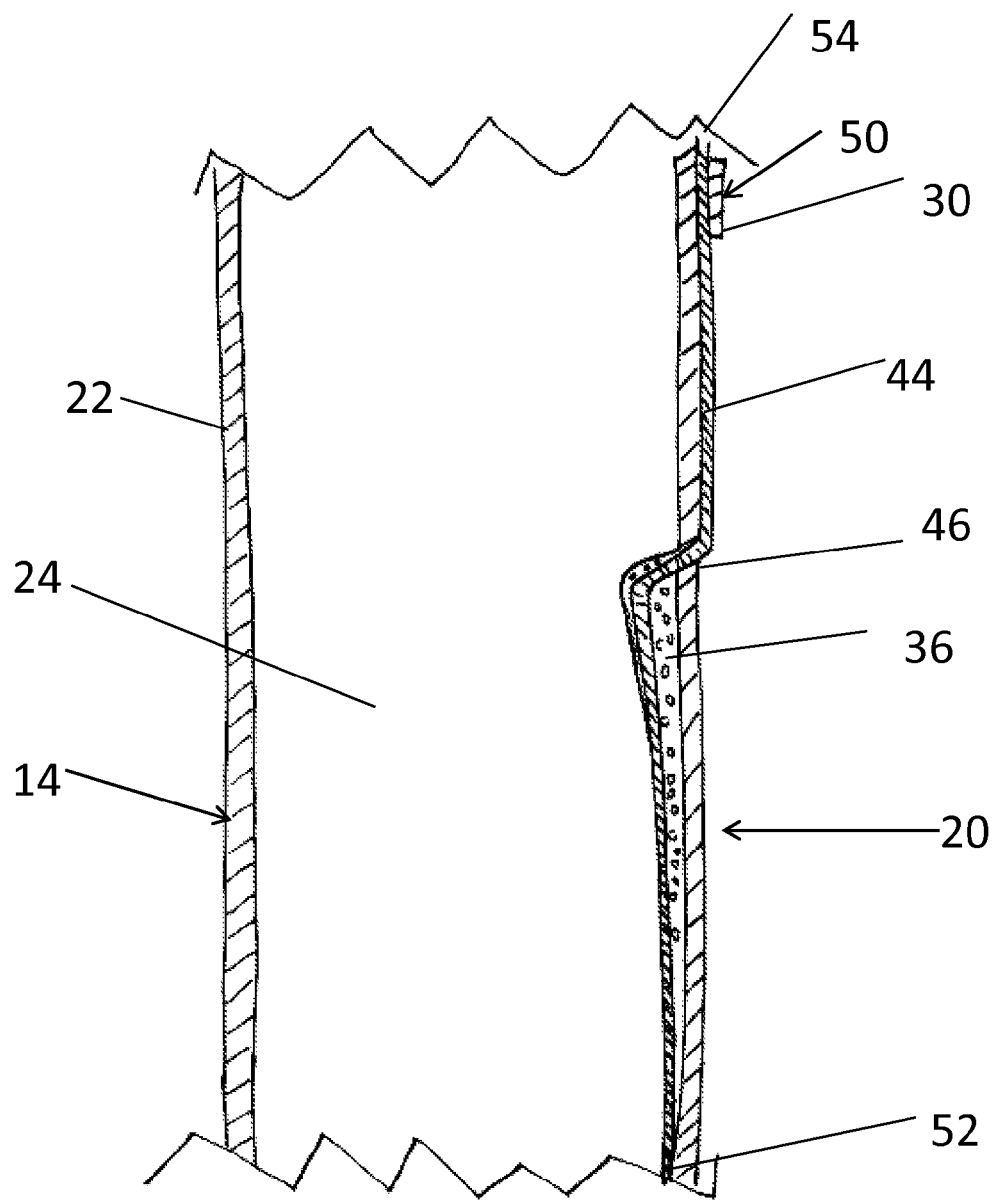

FIGS. 3 and 4 illustrate partially sectional views of a second cleaning component according to an embodiment of the present invention. As illustrated in FIGS. 3 and 4, the second cleaning component 18 includes a sponge 36. The sponge 36 is disposed on a flexible spine 40, which can be formed from a metal, plastic, or other flexible, yet durable material known to or conceivable by one of skill in the art. The flexible spine 40 includes a bend 42 such that a portion 44 of the flexible spine 40 can be extended out of the interior of the trocar shaft 14 through a small opening 46 in the wall 22 of the trocar shaft 14. The portion 44 of the flexible spine 40 that extends outside the interior of the trocar shaft 14 is coupled to the switch 30. The switch 30 is movable between a first position 48 illustrated in FIG. 3 and a second position 50 illustrated in FIG. 4. In the first position 48, the flexible spine 40 is relaxed and the sponge 36 is extended into the middle of the interior of the trocar shaft 14. In the second position 50, the flexible spine 40 is stretched upward and collapses the sponge 36 against the wall 22 of the trocar shaft 14.

More particularly, with respect to FIGS. 3 and 4, and by way of example, which is not meant to be considered limiting, the flexible spine 40 can take the form of a flexible strip of aluminum measuring approximately 3 mm in width. One end 52 of the aluminum strip is attached to an inner wall of the trocar shaft 14. There is a fold or bend 42 in the flexible spine 40, which allows it to form a wedge when fully deployed. The other end 54 is passed through the small opening 46 in the wall 22 of the trocar shaft 14. This end 54 is attached to the switch 30, which can be grooved and configured to slide from the first position 48 to the second position 50 and vice versa.

When the surgeon slides the switch 30 toward the second position 50, this movement pulls the flexible spine 40 flat against the inner wall of the trocar shaft 14. When the surgeon slides the switch toward the first position 48, the flexible spine 40 returns to it slightly wedge shaped configuration, allowing the sponge 36 to deploy towards the center of the trocar shaft 14. The sponge can be formed from any soft, durable material known to or conceivable by one of skill in the art and suitable for removing liquid and condensation from the scope lens. It should also be noted that the movement of the switch 30 into the second position 50, also serves to wring excess liquid from the sponge, such that the sponge can be used repeatedly to remove liquid and condensation from the scope lens.

Figure 5:
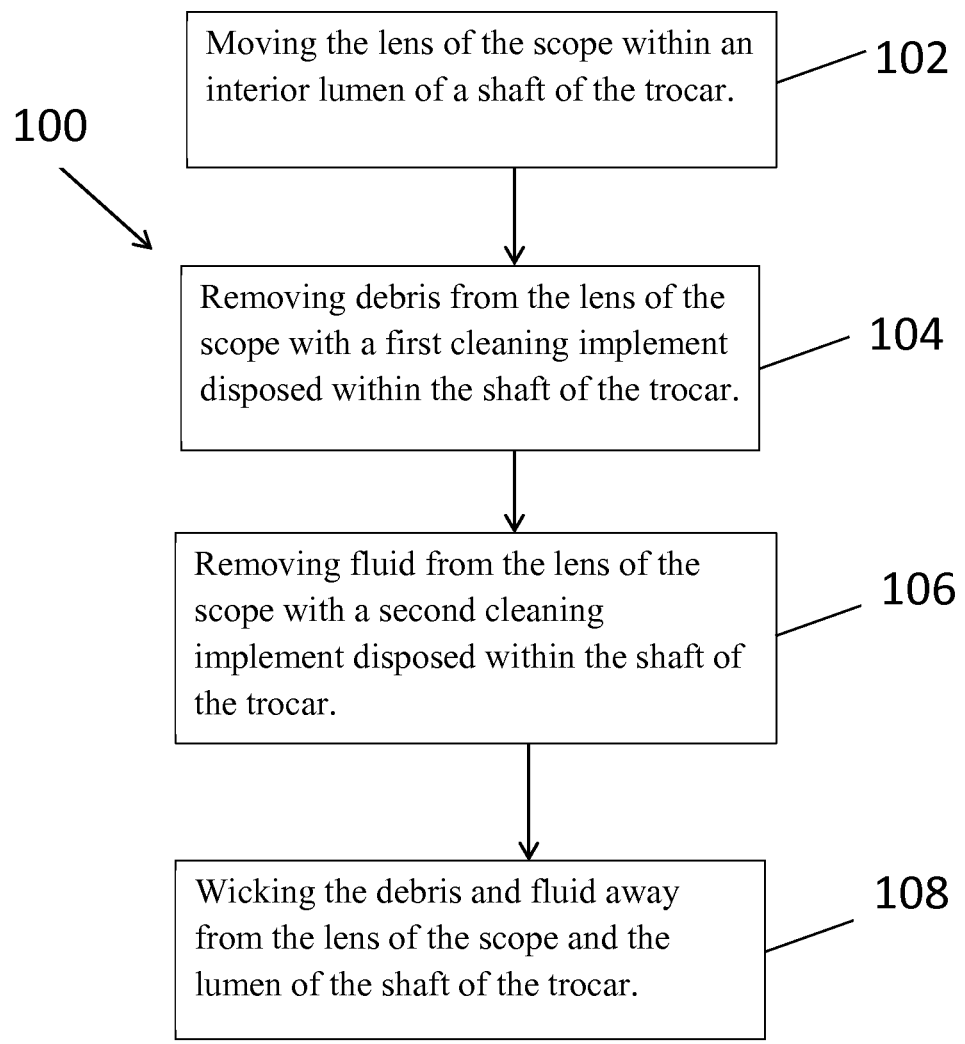
FIG. 5 illustrates a flow diagram of a method of cleaning a scope lens according to an embodiment of the present invention.

FIG. 5 illustrates a flow diagram of a method of cleaning a scope lens according to an embodiment of the present invention. The method 100 for cleaning a lens of a scope configured for use in a trocar includes a step 102 of moving the lens of the scope within an interior lumen of a shaft of the trocar. The method can also include a step 104 of removing debris from the lens of the scope with a first cleaning implement disposed within the shaft of the trocar. Additionally, step 106 includes removing fluid from the lens of the scope with a second cleaning implement disposed within the shaft of the trocar. The method also includes step 108 of wicking the debris and fluid away from the lens of the scope and the lumen of the shaft of the trocar. This way the scope can be moved within the lumen of the shaft of the trocar without re-staining the lens of the scope with the debris or the fluid. The method can further include injecting saline through the first cleaning component to further clean the debris from the lens. An anti-fogging agent can also be injected through the first cleaning component to reduce condensation on the lens of the scope.

An example of the trocar with incorporated scope lens cleaning system is included herein to further illustrate the operation and design of the device. This example is not meant to be limiting and the device can be used for any surgical procedure conceivable by or known to one of skill in the art. During a laparoscopic dissection of an inflamed gallbladder, the surgeon is likely to get blood and fatty tissue on the scope lens. The view of the surgical field is obstructed by this staining, and the surgeon pulls the scope back into the trocar shaft having the incorporated cleaning system. The physician keeps pulling the scope back until the lens is debrided of the solid debris by the brush, positioned closer to the proximal, or physician end of the trocar.

The physician moistens the brush by injecting saline into a side port on the trocar shaft, which is coupled to a spigot disposed at the center of the brush. The physician twists the scope to clean off all of the accumulated debris and the saline jet washes away the debris that accumulates within the trocar shaft. This effluent flows down the trocar past the collapsed sponge and empties quickly due to the grooves in the tip of the trocar. While the lens is clean of blood and fatty debris, but has fluid droplets and condensation on it. The surgeon can then inject an anti-fogging solution through the saline port to apply onto the lens.

Afterwards, he slides the scope in further to the collapsible sponge. He deploys the sponge by sliding the switch at the trocar head. The sponge extends to the middle of the trocar center and the surgeon wipes the lens on the sponge by turning the scope back and forth to allow thorough cleaning of fluid as well as any remaining small debris from the lens. The sponge is then re-collapsed by sliding the switch the other direction. This removes the accumulated fluid within the sponge and creates more space for the scope to pass. Having a newly cleaned lens, the surgeon is now ready to insert the scope back into the operative field and continue the surgery.

The entire cleaning process can take less than 10 seconds to complete. If the surgeon notices that there is a small amount of debris still left within the center of the trocar and does not want to re-stain his lens, he can inject more saline through the brush spigot. The saline will flow down the trocar around his lens and clean out the trocar. During this process, if there is fluid accumulation on the lens, the surgeon can re-deploy the dry sponge to clean the lens.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A cleaning system integrated into a trocar and configured to clean a lens of a scope to be disposed through the trocar, comprising:
    a first cleaning component disposed within a lumen defined by the trocar configured for removing solid debris from the lens of the scope, such that the lens of the scope and the first cleaning component can be brought into contact, and wherein the first cleaning component comprises a brush having a saline spigot for cleaning the debris from the brush and lens of the scope;
    a second cleaning component disposed within the lumen defined by the trocar configured for wiping fluid from the lens of the scope, such that the lens of the scope and the second cleaning component can be brought into contact, wherein the second cleaning component comprises a sponge, the sponge being configured to collapse against a wall of the lumen defined by the trocar, and wherein a slidable switch is configured to collapse the sponge against the wall of the lumen defined by the trocar; and
    a third cleaning component configured to wick the solid debris and fluid away from the lens of the scope, wherein the third cleaning component is disposed at a distal end of the trocar.

2. The cleaning system of claim 1 further comprising the brush extending approximately halfway into a diameter of the shaft of the trocar.

3. The cleaning system of claim 1 wherein the brush further comprises bristles configured to be elastic enough to allow for passage of tools and the scope.

4. The cleaning system of claim 1 wherein the brush further comprises bristles configured to have tensile strength sufficient to remove the debris from the lens of the scope.

5. The cleaning system of claim 1 wherein the brush further comprises a color such that it is visible and identifiable.

6. The cleaning system of claim 1 further comprising the sponge extending approximately halfway into a diameter of the lumen of a shaft of the trocar.

7. The cleaning system of claim 1 further comprising the sponge collapsing to approximately less than 10% of a circumference of a shaft of the trocar.

8. The cleaning system of claim 1 wherein the sponge further comprises a color such that it is identifiable and visible.

9. The cleaning system of claim 1 wherein the third cleaning component comprises grooves.

10. The cleaning system of claim 9 further comprising at least three grooves.

11. A trocar for performing laparoscopic surgery comprising:
- a housing defining a hub and a trocar shaft, wherein said trocar shaft has a proximal end and a distal end and an outer wall defining a lumen extending therethrough, and wherein the hub is coupled to the proximal end of the trocar shaft;
- an obturator configured to be disposed through an opening in the hub of the trocar and through the lumen of the trocar shaft;
- a first cleaning component disposed within the lumen defined by the trocar configured for removing solid debris from a lens of a scope to be disposed through the lumen and disposed on an inside wall of the trocar, such that the lens of the scope and the first cleaning component can be brought into contact, and wherein the first cleaning component comprises a brush having a saline spigot for cleaning the debris from the brush and lens of the scope;
- a second cleaning component disposed within the lumen defined by the trocar configured for wiping fluid from the lens of the scope disposed on the inside wall of the trocar, such that the lens of the scope and the second cleaning component can be brought into contact, wherein the second cleaning component comprises a sponge, the sponge being configured to collapse against a wall of the lumen defined by the trocar, and wherein a slidable switch is configured to collapse the sponge against the wall of the lumen defined by the trocar; and
- a third cleaning component configured to wick the solid debris and fluid away from the lens of the scope, wherein the third cleaning component is disposed at the distal end of the trocar shaft.

12. The trocar of claim 11 further comprising the brush extending approximately halfway into a diameter of the shaft of the trocar.

13. The trocar of claim 11 wherein the brush further comprises bristles configured to be elastic enough to allow for passage of tools and the scope.

14. The trocar of claim 11 wherein the brush further comprises bristles configured to have tensile strength sufficient to remove the debris from the lens of the scope.

15. The trocar of claim 11 wherein the brush further comprises a color such that it is visible and identifiable.

16. The trocar of claim 11 further comprising the sponge extending approximately halfway into a diameter of the lumen of the trocar shaft.

17. The trocar of claim 11 further comprising the sponge collapsing to approximately less than 10% of a circumference of the shaft of the trocar.

18. The trocar of claim 11 wherein the sponge further comprises a color such that it is identifiable and visible.

19. The trocar of claim 11 wherein the third cleaning component comprises grooves.

20. The trocar of claim 19 further comprising at least three grooves.

* * * * *